(12) United States Patent
Omuro et al.

(10) Patent No.: US 8,603,414 B2
(45) Date of Patent: Dec. 10, 2013

(54) MICRO-CHEMICAL ANALYSIS DEVICE, MICROCHEMICAL MEASURING METHOD, AND SAMPLE COLLECTING TOOL

(75) Inventors: Naoko Omuro, Tochigi-ken (JP); Shoichi Kanayama, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 523 days.

(21) Appl. No.: 12/164,371

(22) Filed: Jun. 30, 2008

(65) Prior Publication Data

US 2009/0004060 A1 Jan. 1, 2009

(30) Foreign Application Priority Data

Jun. 29, 2007 (JP) ................................. 2007-172251

(51) Int. Cl.
*G01N 15/06* (2006.01)
(52) U.S. Cl.
USPC ........... 422/504; 422/502; 422/503; 422/509; 422/50; 422/68.1; 422/81; 436/43; 436/180
(58) Field of Classification Search
USPC ........ 422/50, 68.1, 81, 82, 82.01, 82.02, 100, 422/101, 102, 502, 503, 504, 509; 436/43
See application file for complete search history.

(56) References Cited

U.S. PATENT DOCUMENTS

| 5,008,616 | A | 4/1991 | Lauks et al. | |
|---|---|---|---|---|
| 2004/0086427 | A1* | 5/2004 | Childers et al. | 422/100 |
| 2006/0263265 | A1* | 11/2006 | Kang et al. | 422/101 |
| 2008/0124245 | A1 | 5/2008 | Ito et al. | |

FOREIGN PATENT DOCUMENTS

JP 3351002 9/2002

* cited by examiner

*Primary Examiner* — Brian J Sines
(74) *Attorney, Agent, or Firm* — Oblon, Spivak, McClelland, Maier & Neustadt, L.L.P.

(57) ABSTRACT

A micro-cassette 1 stores a sample, a reagent, and an additive, and comprises a sensor measures the component of measurement item. Analysis device 2 comprises liquid control unit controls each liquid in micro-cassette 1. Mixing controller 33 mixes the sample and the additive sent to sample processing unit 13, and generates the first sample includes a formed element. Isolation unit 14 generates the second sample from the first sample sent from sample processing unit 13. Sensor 18 measures the compound liquid of the second sample and reagent, and generates the analysis signal.

12 Claims, 15 Drawing Sheets

_US 8,603,414 B2_

MICRO-CHEMICAL ANALYSIS DEVICE, MICROCHEMICAL MEASURING METHOD, AND SAMPLE COLLECTING TOOL

CROSS-REFERENCE TO RELATED APPLICATIONS

This application is based upon and claims the benefit of priority from prior Japanese Patent Application No. 2007-172251, filed Jun. 29, 2007, the entire contents of which are incorporated herein by reference.

BACKGROUND OF THE INVENTION

1. Field of the Invention

The present invention relates to a micro-chemical analysis device used to analyze components contained in a liquid, and a method of measuring the micro-chemical and, more particularly, to a micro-chemical analysis device for analyzing components contained in human blood or urine, and a method of measuring the micro-chemical analysis.

2. Description of the Related Art

The chemical analysis device mixes a sample such as blood and urine obtained from subject and a reagent that corresponds to each measurement item contained in this object to be examined, and a density and an enzymic activity of various components in the sample are measured by a change of a tone etc. that occur because of the chemical reaction of the compound liquid. Additionally, the chemical analysis device measures density of various components in sample with sensors such as the ion sensors and the enzyme sensors that selectively respond to the component of the measurement item contained in sample.

In recent years, the chemical analysis device has become smaller in size. For example, there have been proposed a mobile chemical analysis device using a sheet-type micro reactor that can do the blood test and the chemical reaction disclosed in Japanese unexamined patent publication NO. 2002-340911. In this device, the micro reactor that injects blood that is the sample is mounted in a main body of the device, the mounted micro reactor is rotated, and blood is separated to a blood corpuscle and a blood plasma by centrifugal separation. In addition, the blood plasma that separates in the micro reactor moves to a reaction tank through a minute channel. A reaction liquid of the blood plasma and the reagent in the reaction tank is measured by using a light emission element and a light detecting element put in the main body of the device.

However, the viscosity of the sample such as blood that contains a protein, a lipid, and a carbohydrate, etc. is high. Therefore, it is difficult that sending the sample to the micro channel like the micro reactor and mixing with a sent sample and the reagent, there is a problem that it negatively affects the measurement.

BRIEF SUMMARY OF THE INVENTION

Accordingly, an advantage of an aspect of the present invention is to provide the micro-chemical analysis device, micro-chemical measuring method, and sample collecting tool can weed out a useless formed element negatively affects measurement of the sample.

In order to achieve the above-described advantage, a first aspect of the invention may comprise a detachable micro-cassette containing an original sample and a reagent, an analysis device configured to receive the detachable micro-cassette containing an original sample and a reagent, a sample processing unit configured to mix an additive to the original sample to obtain a first sample and a removable material, an isolation unit configured to separate the removable material from the first sample to produce an isolated second sample, and data processing unit configured to produce analysis data indicative of a component of interest included in a mixture of the isolated sample and the reagent.

Further, another aspect of the invention may comprise generating a first sample and a removable material by mix an additive to the original sample to obtain in micro-cassette, generating a second sample to separate the removable material from the first sample, mixing the compound liquid of the second sample and a reagent is stored in the micro-cassette, and generating analysis data to measure the compound liquid in an analysis device.

Further, another aspect of the invention may comprise a needle collects a sample, a cylinder stores the sample through the needle, a piston flows in the sample into the cylinder and flows out the sample is flowed, an additive generates a first sample that a predefined component in the sample is corporealized moving the piston, a filtration film generates a second sample isolating a formed element in the first sample moving the piston.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, each embodiment of the micro-chemical analysis device according to the present invention will be described in detail with reference to the drawings.

Embodiment 1

Figure 1:
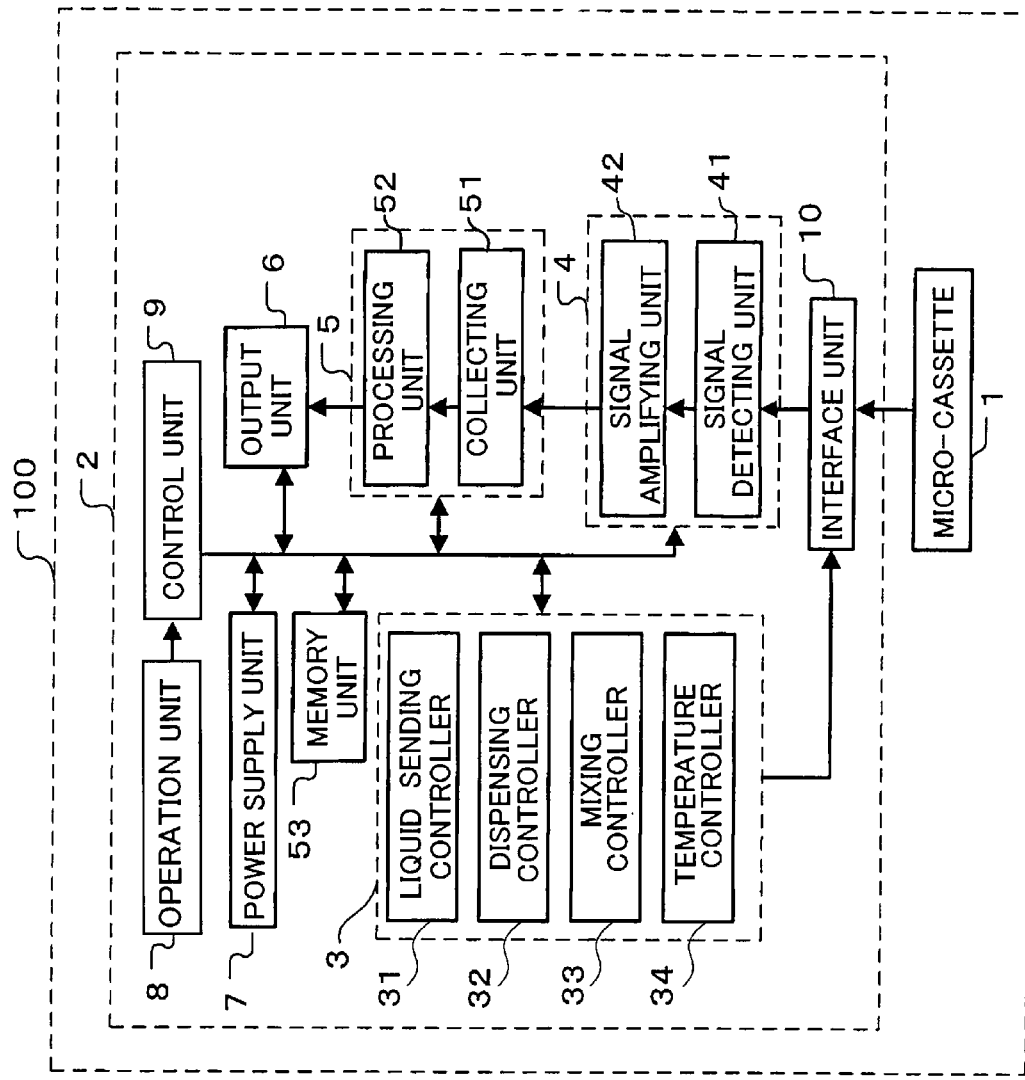
FIG. 1 is a block diagram showing a configuration of a micro-chemical analysis device according to the first embodiment.
Figure 2:
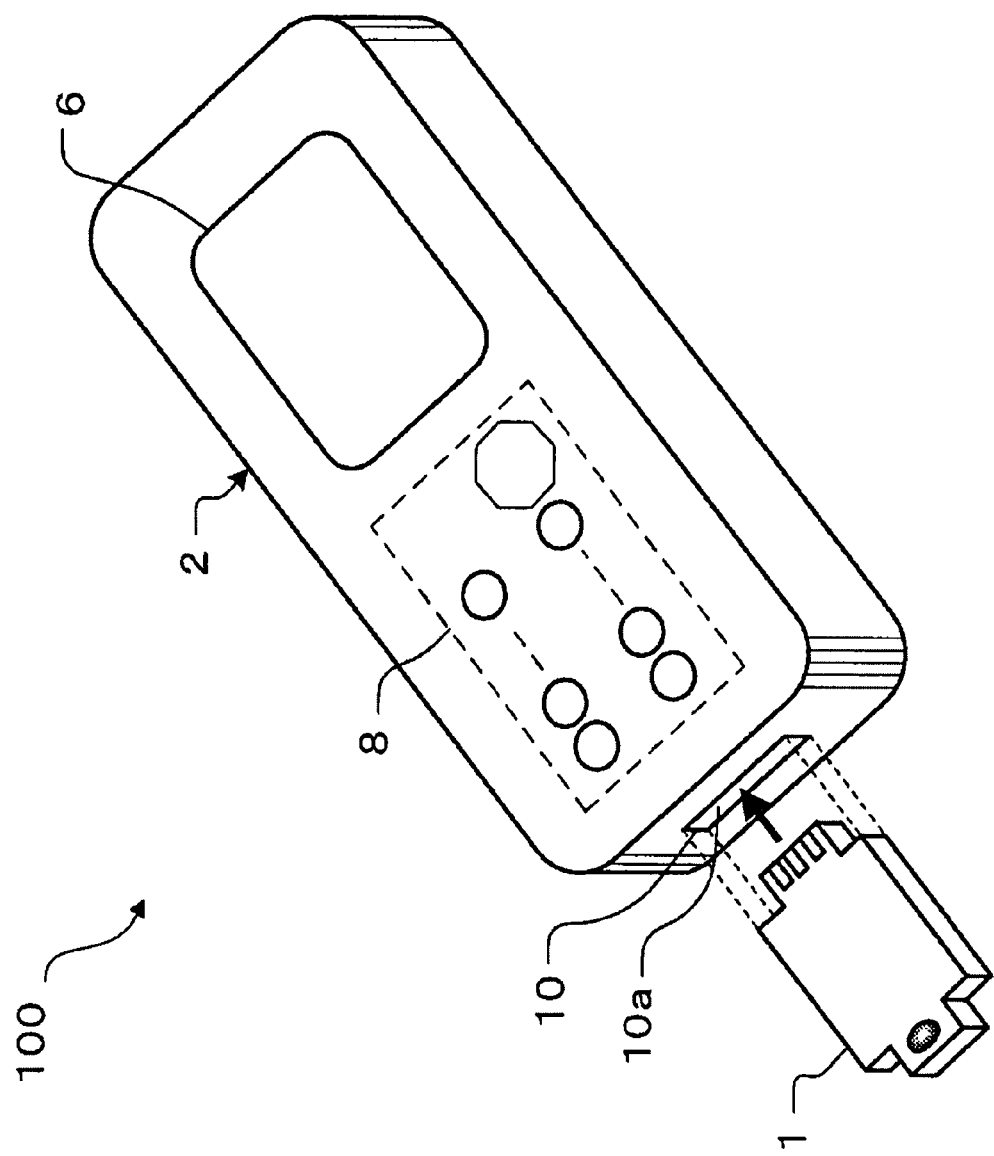
FIG. 2 is a diagram showing an appearance of a micro-chemical analysis device according to the first embodiment.

FIG. 1 is a block diagram showing a configuration of a micro-chemical analysis device according to the first embodiment. FIG. 2 is a diagram showing an appearance of a micro-chemical analysis device according to the first embodiment.

A micro-chemical analysis device 100 as shown in FIG. 1 generally comprises a sample taken from a subject, an additive for dispose of an undesirable useless component in the sample negatively affects measurement, a micro-cassette 1 that accommodates reagent that corresponds to measurement item of sample, an analysis device 2 that generates an analysis data detecting signal generated with measurement of micro-cassette 1.

Analysis device 2 is portable size. Analysis device 2 comprises an interface unit 10 maintains micro-cassette 1, a liquid control unit 3 controls each liquid accommodated in micro-cassette 1, a detection unit 4 detects signal from micro-cassette 1, a data processing unit 5 generates analysis data from detection signal detected in detection unit 4.

Analysis device 2 comprises a memory unit 53 preserves analysis data generated in data processing unit 5, an output unit 6 outputs analysis data generated in data processing unit 5, a power supply unit 7 supplies an electric power to each unit of analysis device 2 such as a liquid control unit 3, the detection unit 4, and data processing unit 5, an operation unit 8 is input various command signals, a control unit 9 controls each unit as referred to above.

Interface unit 10 bears an opening 10a as shown in FIG. 2. The micro cassette is inserted in opening 10a, and fixed in the free detachment by analysis device 2.

Liquid control unit 3 comprises a liquid sending controller 31 delivers each liquid in micro-cassette 1 retained in interface unit 10, a dispensing controller 32 dispenses the sample processed by the additive, a mixing controller 33 mixes a compound liquid of the sample to which the additive was added or dispensed the sample and the reagent, a temperature controller 34 configures the compound liquid at a predefined temperature.

Liquid sending controller 31 delivers each liquid corresponding to each storage unit of the micro-cassette that accommodates each liquid of the sample, the additive, and the reagent. For example, each liquid is delivered depressing a upper surface in each storage unit. The actuator like a piezoelectric element is mounted on, the upper surface corresponding to each storage unit where the actuator accommodates each liquid of micro-cassette 1 is vibrated by a predefined frequency. The vibration pressurizes or decompresses in each storage unit, as a result, each liquid is sent. The liquid sending method includes Difuza method to send liquid according to impedance difference of each channel on entrance side and exit side of pup chamber fixed in each storage unit and method to provide with check valve in each unit in micro-cassette 1 etc.

For example, dispensing controller 32 dispenses the sample processed by the additive in micro-cassette 1 as well as liquid sending controller 31.

For example, mixing controller 33 vibrates from the upper surface of micro cassette 1, and mixes the compound liquid of the sample to which the additive in micro-cassette 1 was added or dispensed the sample and the reagent.

Temperature controller 34 comprises a heater and a radiator, and it is allocated near micro-cassette 1 maintained in interface unit 10, and configures at a predefined temperature and maintains the compound liquid of the sample and the reagent.

Detection unit 4 comprises a signal detection unit 41 detects a signal output from micro-cassette 1 maintained in the interface unit 10, a signal amplifying unit 42 amplifies to a predefined signal level a detection signal from signal detection unit 41. Detection unit 4 outputs the detection signal amplified in signal amplifying unit 42 to data processing unit 5.

Date processing unit 5 comprises a collecting unit 51 generates a subject data from the detection signal output from signal amplifying unit 42 of detection unit 51, a processing unit 52 generates an analysis data from the subject data generated in collecting unit 51.

Collecting unit 51 comprises an analog digital converter (ADC), and an analog signal that is the detection signal output from signal amplifying unit 42 is converted into a digital signal by using ADC, and the converted digital signal is output to processing unit 52 as subject data.

Processing unit 52 reads out a calibration table of the measurement item preserved in memory unit 53 to the subject data output from collecting unit 51, the analysis data of a constituent concentration etc. of the measurement item of the sample is generated by using the calibration table. Processing unit 52 output to output unit 6 the generated analysis data and it is preserved in memory unit 53.

Memory unit 53 comprises a memory circuit, and preserves the analysis data output from processing unit 52 and an input data input from operation unit 8. Memory unit 53 preserves the calibration table used to generate the analysis data.

Output unit 6 comprises a monitor such as liquid crystal panels, and displays the analysis data output from processing unit 52 in the data processing unit 5. The aforementioned method of the display other than may be used. For example, Sight transmission means using lighting display light or, aural transmission means using aural by voice. Two or more means may be used together.

Power supply unit 7 may comprises a electrifiable storage battery, and supplies an electric power to each unit such as liquid control unit 3, detection unit 4, data processing unit 5, memory unit 53, output unit 6, operation unit 8, and control unit 9.

Operation unit 8 comprises an input device such as buttons on an operation panel, and implements operation such as on-off system of the power supply, input of subject information, measurement operation of the sample accommodated in micro-cassette 1, output of a variety of analysis data preserved in memory unit 53.

Control unit 9 controls each unit in liquid control unit 3, detection unit 4, data processing unit 5, memory unit 53, output unit 6, and power supply unit 7 based on input information from operation unit 8, and overall controls an entire system.

Figure 3:
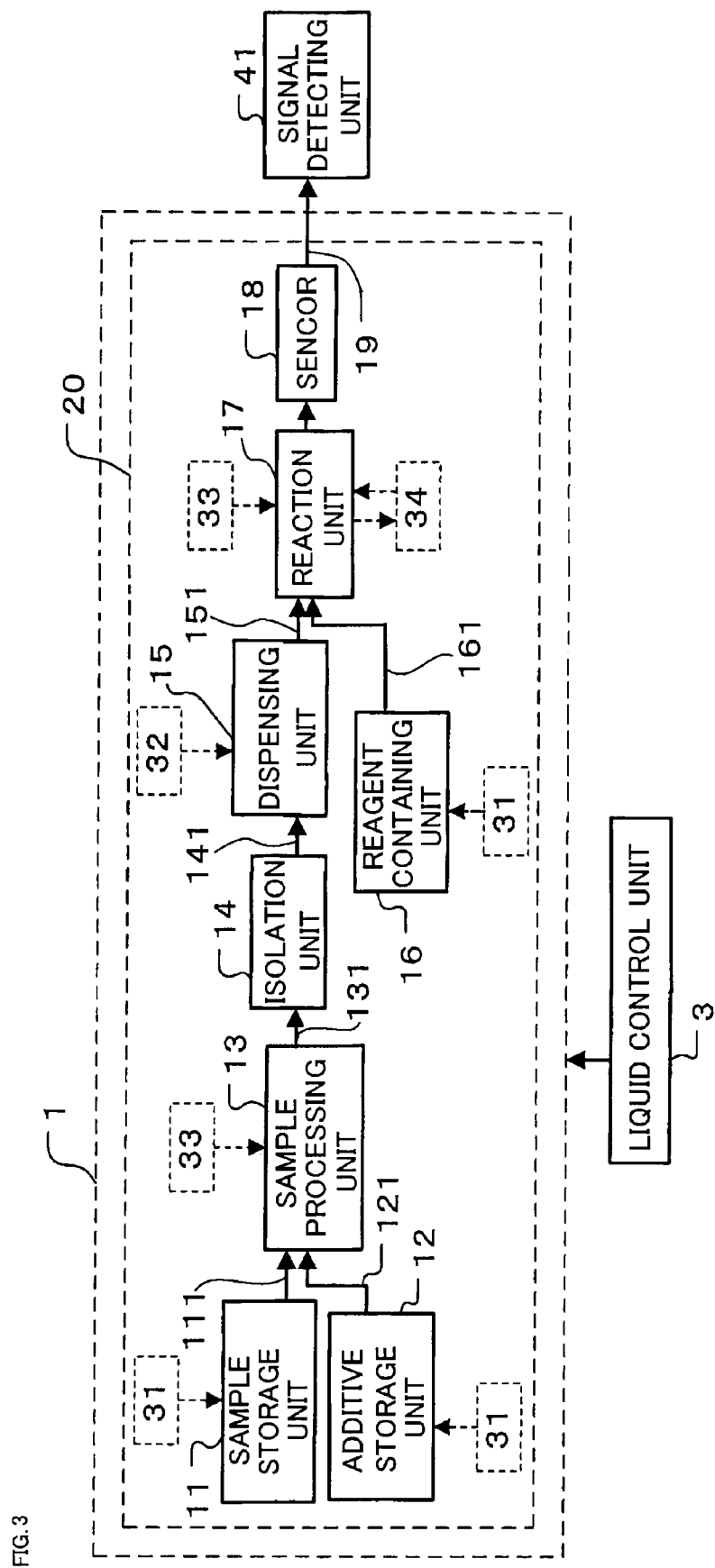
FIG. 3 is a view showing a configuration of a micro-cassette according to the first embodiment.
Figure 4:
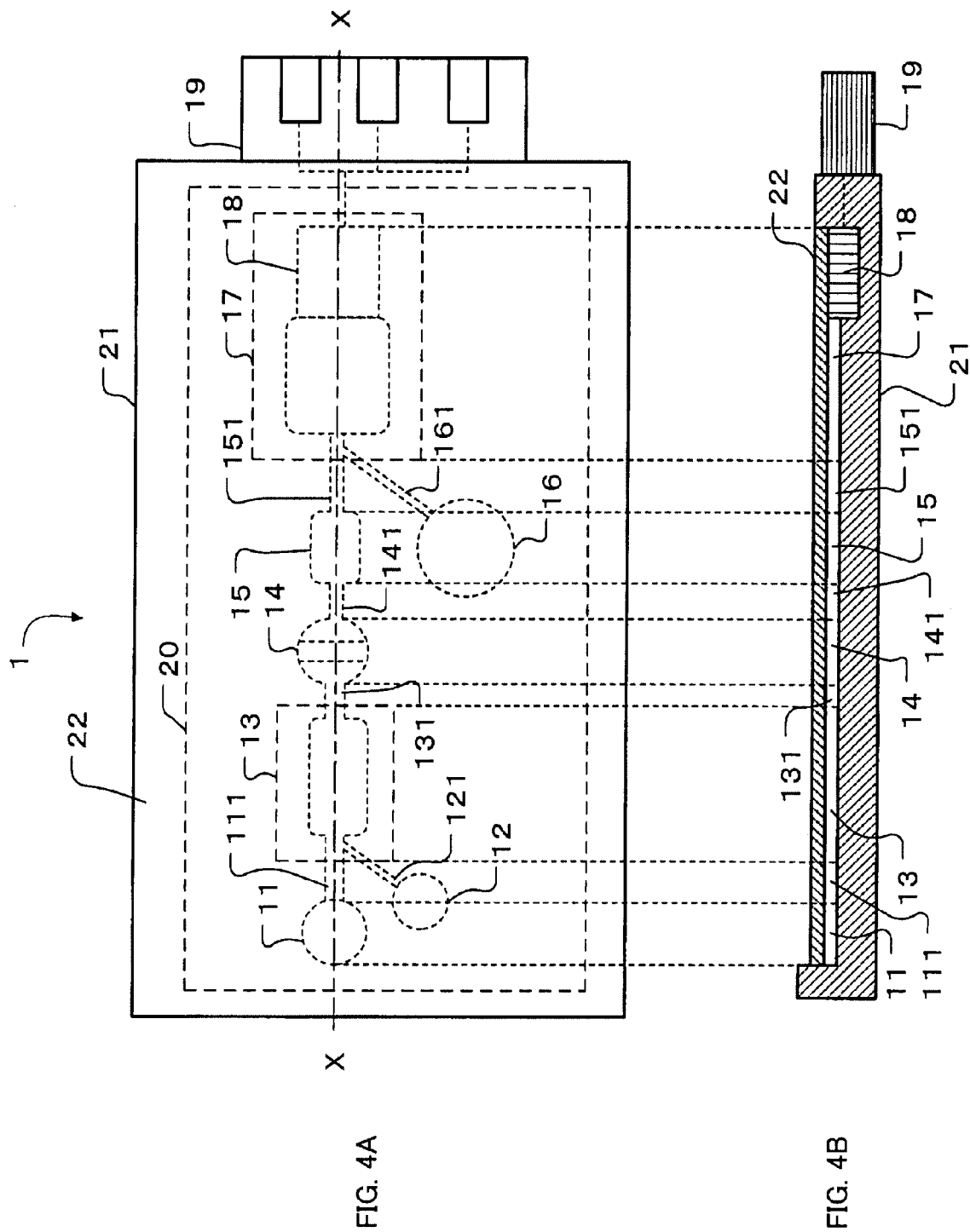
FIG. 4A is a top view of a micro-cassette according to the first embodiment.
FIG. 4B is a cross-section showing of a micro-cassette according to the first embodiment.

Next, details of micro-cassette 1 will be explained with reference of FIGS. 1 to 4. FIG. 3 is a view showing a configuration of a micro-cassette. FIG. 4A is a top view of a micro-cassette, and FIG. 4B is a cross-section of D-D line in FIG. 4 showing of a micro-cassette.

Micro-cassette 1 comprises each storage unit where the upper surface such as fused silica, silicon, plastic, and ceramics is formed through microfabrication, and it accommodates each liquid of sample, additive, and reagent. Micro-cassette 1 comprises a base material 21 (FIG. 4) has an analysis unit 20 is composed by each minute channel where be communicated with each storage unit as indicated by arrow line (FIG. 3), and a seat 22 is connected on base material.

Analysis unit 20 comprises a sample storage unit 11 stores the sample injected in micro-cassette 1, an additive storage unit 12 stores the additive that corporealize reacting with the useless component negatively affects the measurement in the sample, a sample processing unit 13 generates a first sample by adding and processing the additive to the sample, and an isolation unit 14 removes the formed element contained in the first sample generated in the sample processing unit 13 and generates a second sample.

Analysis unit 20 comprises dispensing unit 15 dispenses the second sample generated in isolation unit 14, a reagent storage unit 16 stores the reagent that corresponds to the measurement item of the sample, a reaction unit 17 measures the compound liquid of the second sample dispensed from dispensing unit 15 and the reagent in reagent storage unit 16 by using sensor 18, and a connector outputs a signal that is generated by a measurement by sensor 18 to analysis device 2.

There is an opening in an upper side in the sample storage unit 11, and the opening is covered with seat 22. As for an injection part where the sample of seat 22 is injected, a material of an elastic body that prevents leaking the sample to outside of micro-cassette 1 and secures sealing performance may be used. Sample storage unit 11 leads to sample processing unit 13 through a sample channel 111. For example, the sample of the amount to which sample storage unit 11 where the sample of 0.1 to 50 μL was stored is set beforehand is sent to sample processing unit 13 by liquid sending controller 31 in liquid controller 3 of analysis device 2 through sample channel 111.

For example, when the sample is blood, a formed element such as a blood corpuscle and fibrin with elements such as a protein, lipids, and carbohydrate that become factor of a high viscosity for instance that negatively affect the measurement are contained. Sample channel 111 cut back the length of the channel compared with other channels and it is enlarges the diameter so that smooth liquid sending the sample is possible.

Additive storage unit 12 stores various additives in state of selectable. For example, the additive make the formed element by denaturation and agglomeration from the useless component that negatively effects the measurement contained in the sample. Additive storage unit 12 leads to sample processing unit 13 through an additive channel 121. The additive of the amount set beforehand is sent from additive storage unit 12 to sample processing unit 13 with liquid sending unit synchronizing with a sending motion of the sample.

The protein in the sample has characteristic of a high viscosity. The protein in the sample that has the characteristic of a high viscosity can make it make to material by using additives such as metaphosphoric acid and ethanol. For example, it becomes the factor that the liquid sending speed of each channel of the compound liquid of the sample and reagent, and the sample is decreased for a high viscosity, and a predefined amount cannot be sent, and it becomes the factor that to disturb making of uniform the compound liquid of the sample and the reagent.

Sample processing unit 13 has formed a Y-shaped that joins sample channel 111 and addition channel 121. Sample processing unit 13 leads to isolation unit 14 through a processing channel 131 formed on the opposite side of sample channel 111.

The additive is added at Y-shaped channel in the sample processing unit 13 synchronizing with the sending operation of the sample. The sample to which the additive is added becomes uniform being mixed the additive and the sample by the mixing controller 33. The first sample is generated that predefined component in the component contained in the sample is corporealized. The first generated sample is sent to the isolation unit 14 through the processing channel 131.

Analysis unit 20 may comprises the second sample processing unit between sample processing unit 13 and isolation unit 14, and the second additive storage unit accommodates the second additive to process the first sample in second sample processing unit. The first sample may be sent to isolation unit 14 that the first sample did processing that is corporealized a different component in the second sample processing unit.

A useless component by the measurement in the sample picked from subjects can be corporealized.

Isolation unit 14 comprises filtration to separate the formed elements is generated in sample processing unit 13 and to separate other formed elements contained in the sample when stored in sample storage unit 11. Isolation unit 14 leads to a dispensing unit 15 through a isolation channel 141 formed on the opposite side of processing channel 131. Isolation unit 14 generates the second sample that is weed out the formed element in the first sample by passing the filtration firm. The second sample is sent to dispensing unit 15 through isolation channel 141.

Analysis unit 20 comprises a second isolation unit at sample storage unit 11 or between sample storage unit 11 and sample processing unit 13. The second isolation unit may weed out a formed element such as fibrin and a blood corpuscle in the sample picked from subject. Afterwards, may generate the first sample in sample processing unit 13.

As a result, a useless formed element can be weed out to measurement of the first sample. If the second sample is a sample to which a high-density protein is weeded out, the second sample decreases viscosity can be sent to dispensing unit 15 by being smoothly pass isolation channel 141 in a short time.

Dispensing unit 15 stores the second sample once sent from isolation unit 14. Dispensing unit 15 leads to reaction unit 17 through a reaction channel 151. The amount of the second sample is set beforehand is sent to reaction unit 17 through dispensing channel 151 by dispensing controller 32. If the second sample is a sample to which a high-density protein is weeded out so the viscosity decreases, the amount of the second sample is set beforehand accurately can be sent to a reaction unit 17.

Reagent storage unit 16 stores the reagent that corresponds to the measurement item, and leads to reaction unit 17 through a reagent channel 161. Liquid sending controller 31 that synchronizes with dispensing motion of the second sample sends the amount of the regent in reagent storage unit 16 set beforehand to reaction unit 17. For example, if there are two kinds of reagent of the measurement item, analysis unit 20 comprises a second reagent storage unit where it stores the second reagent and leads to reaction unit 17 through a second reagent channel. After the reagent is sent from reagent storage unit 16 to reaction unit 17, liquid sending controller 31 may send the second reagent from the second reagent unit to reaction unit 17.

Reaction unit 17 has formed a Y-shaped that joins dispensing channel 151 and reagent channel 161. Reaction unit 17 comprises sensor such as the ion selective equipment selectively senses to the electrolyte such as sodium ions, ion sensor composed by reference electrode that becomes standard of the electrode, and enzyme sensor from which polymer membrane is made immobilization includes glcosokisidarze (GOD) that selectively reacts to measurement component such as glucoses. After the reagent joins the second sample at Y-shaped in reaction unit and is mixed, a compound liquid is mixed by mixing controller 33, and uniformize.

If the viscosity of the second sample decrease by weeding out the protein in the sample, it becomes easy to distribute the second sample and reagent in Y-shaped. Molecular diffusion of the second sample and reagent mutually distributed by the mixing motion by the mixing controller expeditiously come off, and an uniformize compound liquid can be obtained.

The compound liquid mixed in a reaction unit 17 is maintained at a predefined temperature by temperature controller 34 of the liquid controller 3 in analysis device 2 located near the micro-cassette 1. Afterwards, the compound liquid is measured with sensor. Sensor 18 generates the signal corresponding to the density of the component of the measurement item, and the generated signal is output to signal detection unit 41 of detection unit 4 in analysis device 2 through a connector. The sample, the additive, the reagent, and the compound liquid after the measurement ends are maintained in the micro-cassette 1.

It can prevent pollution of operator and analysis device 2 from each liquid, because each liquid used for the measurement is maintained in micro-cassette 1.

One example of motion of micro-chemical analysis device 100 in accordance with first embodiment will be explained with reference to FIGS. 1 to 5.

Figure 5:
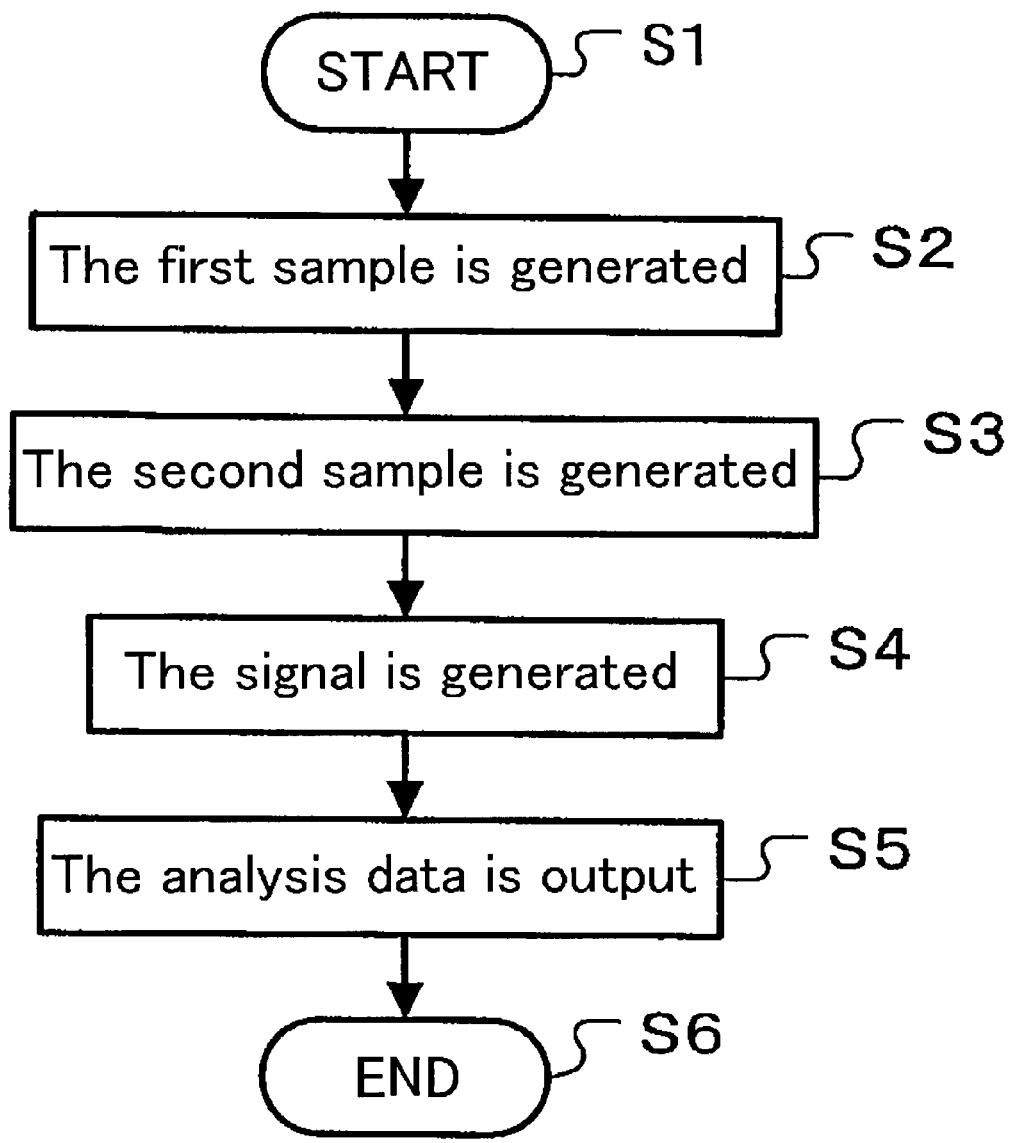
FIG. 5 is a flow chart showing an operation of a micro-chemical analysis device according to the first embodiment.

FIG. 5 is a flow chart showing an operation of a micro-chemical analysis device according to the first embodiment. An operator turns on power from operation unit 8 of micro-chemical analysis device 100, and input subject information on subject. The operator inserts micro-cassette 1 where the sample of subject is stored in the opening 10a in the interface unit 10 in analysis device 2. Afterwards, the operator does the measurement operation from operation unit 8, and micro-chemical analysis device begins measuring (S01).

Control unit 9 directs liquid control unit 3, detection unit 4, data processing unit 5, memory unit 53, and output unit 6 to measure based on input information from operation unit 8. Liquid sending controller 31, dispensing controller 32, mixing controller 33, and temperature controller 34 in liquid control unit 3 controls each liquid in micro-cassette 1.

Liquid sending controller 31 sends the sample of sample storage unit 11 and additive of additive storage unit 12 in micro-cassette 1 respectively through sample channel 111 and the additive channel 121. Mixing controller 33 mixes the sample and additive sent to sample processing unit 13, and generates the first sample (S02).

Liquid sending controller 31 sends the first sample generated in sample processing unit 13 to isolation unit 14 through processing channel 131. Isolation unit 14 generates the second sample from the first sample sent from sample processing unit 13 (S03).

The second sample generated in the isolation unit 14 is dent to dispensing unit 15 through isolation channel 141.

Dispensing controller 32 dispenses the second sample from isolation unit 14 to reaction unit 17 through dispensing channel 151, and liquid sending controller 31 sends the reagent in reagent storage unit 16 to reaction unit 17 through reagent channel 161.

Mixing controller 33 mixes the compound liquid of the reagent sent from reagent storage unit 16 and the second sample sent from dispensing unit 15 to reaction unit 17. Temperature controller 34 sets at a predefined temperature and maintains the compound liquid. Sensor 18 generates the signal corresponding to the component density of the measurement item by measures the compound liquid maintained at a predefined temperature. Sensor 18 outputs the generated signal to detection unit 4 of analysis device 2 through connector 19 (S04).

Signal detection unit 41 of detection unit 4 outputs to the signal amplifying unit 42 detecting the signal output through connector 19 of micro-cassette 1. Signal amplifying unit 42 amplified the detection signal output from the signal detection unit 41 to a predefined signal level and is output to the data processing part.

A collecting unit 51 in data processing unit generates the subject data from the detection signal output from signal amplifying unit 42, and outputs it to processing unit 52. Processing unit 52 reads out the calibration table of the measurement item from memory unit 53 to the subject data output from collecting unit 51. Processing part 52 generates the analysis data such as the component density of the measurement item included in the sample by using the read out calibration table, and preserves the generated analysis data in memory unit 53 and output to output unit 6 (S05).

When the analysis data is output to the out put unit 6, controller 9 directs liquid control unit 3, detection unit 4, data processing unit 5, memory unit 53, and output unit 6 to stop of the measurement operation, and microanalysis device is concluded the measurement (S06).

After the measurement is concluded, operator removes micro-cassette 1 where each liquid that is concluded measurement is stored from analysis device 2, and scraps micro-cassette 1 taken out.

Figure 6:
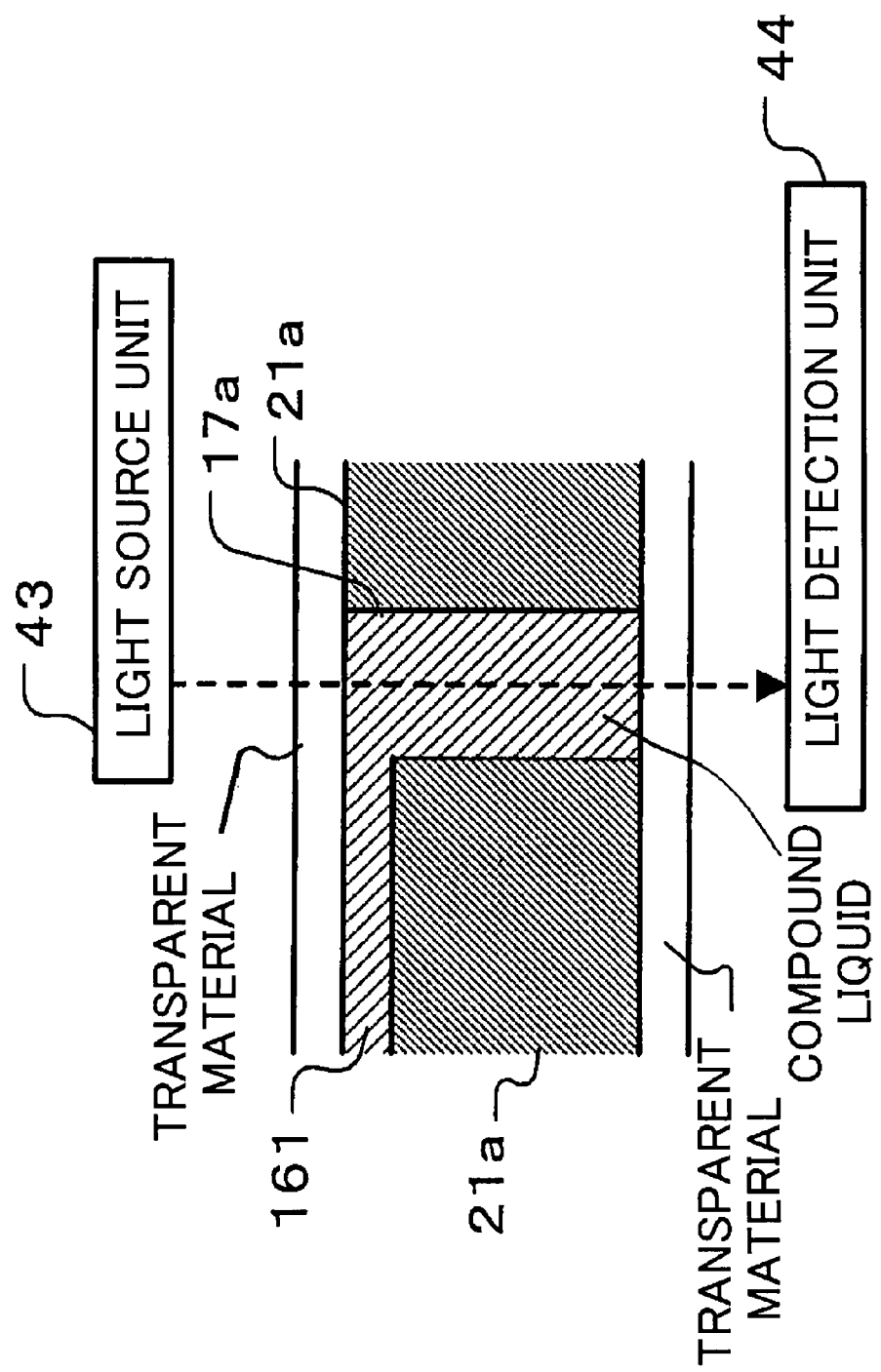
FIG. 6 is a view showing the other configuration of a micro-cassette according to the first embodiment.

As shown in FIG. 6, for example, analysis device 2 may comprises light source unit that has semiconductor laser and light emitting diode in detection unit 4, and replaces the signal detection unit 41 with the photodetection unit has the light detecting element such as the photodiode that detects light from light source unit. The micro-cassette 1 may connect transparent materials that penetrate light from the light source unit 43 the upper and downward surface in the reaction unit 17a that penetrated through the substrate and was formed. The reagent for an optical measurement is stored in this micro-cassette 1. Light from light source unit 43 is irradiated to the compound liquid of the sample and the reagent that reacts in reaction unit 17a. Light that penetrates the compound liquid is measured detecting it in light detection unit 44. As a result, the component of the measurement item of the sample that cannot be measured with sensor 18 can be measured.

Figure 7:
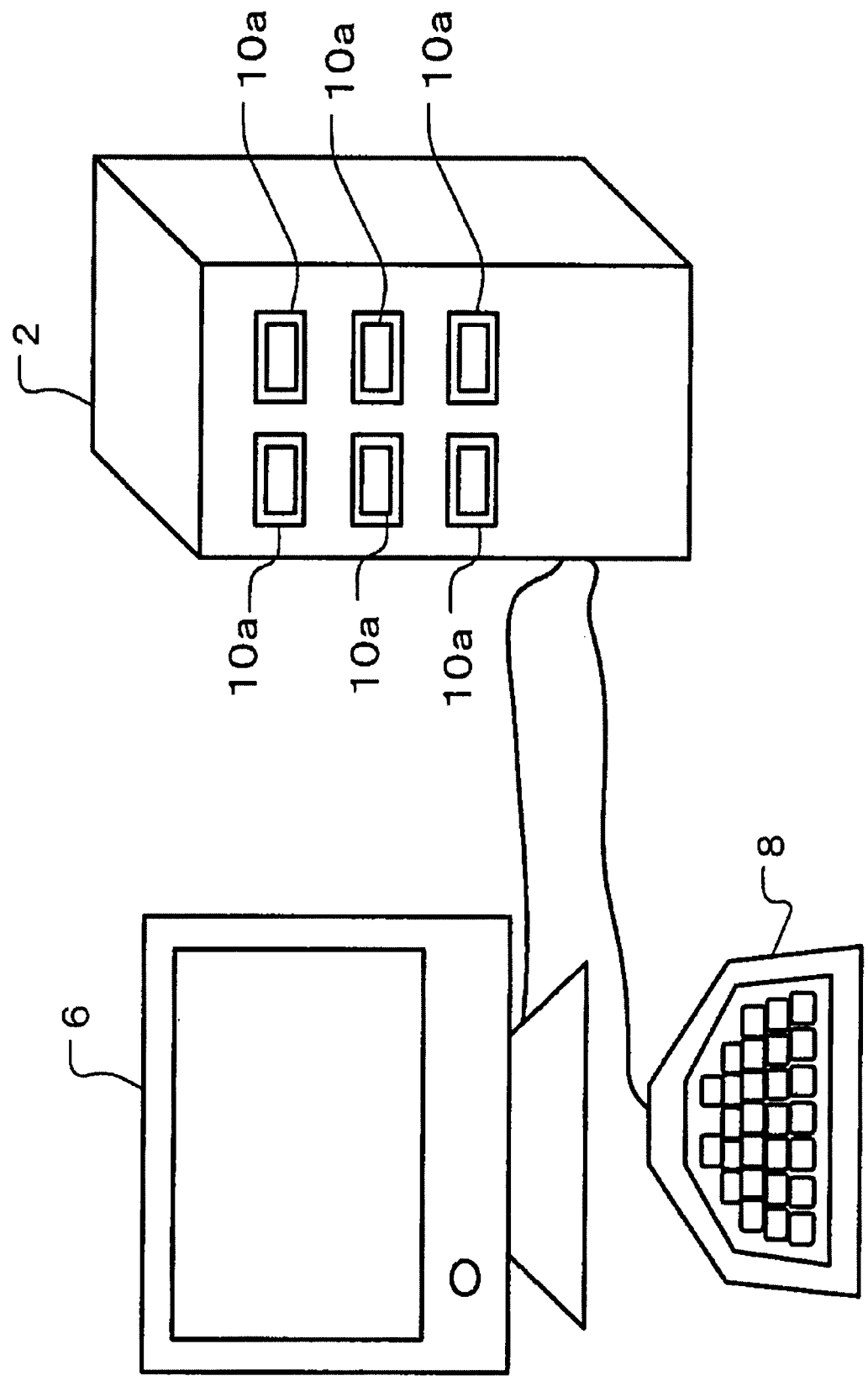
FIG. 7 is a view showing the other configuration of a micro-chemical analysis device according to the first embodiment.

As shown in FIG. 7, analysis device 2 may comprise opening 10a that forms two or more interface unit, the liquid control unit and detection unit are arranged to correspond to each interface unit. As a result, the sample gathered from plural subjects can be measured at the same time.

Micro-chemical analysis device 100 can measure the component of plural measurement items at the same time for the sample gathered from subject with plural micro-cassette 1 with a different measurement item. In this case, as shown in FIG. 7, a display unit and an operation unit may be established separating from analysis device.

Plural analysis units are established on the substrate of micro-cassette 1 so that the measurement of plural measurement items or plural samples is possible. Plural measurement items or plural samples can be measured at the same time by comprising liquid control unit corresponding to plural analysis device.

Figure 8:
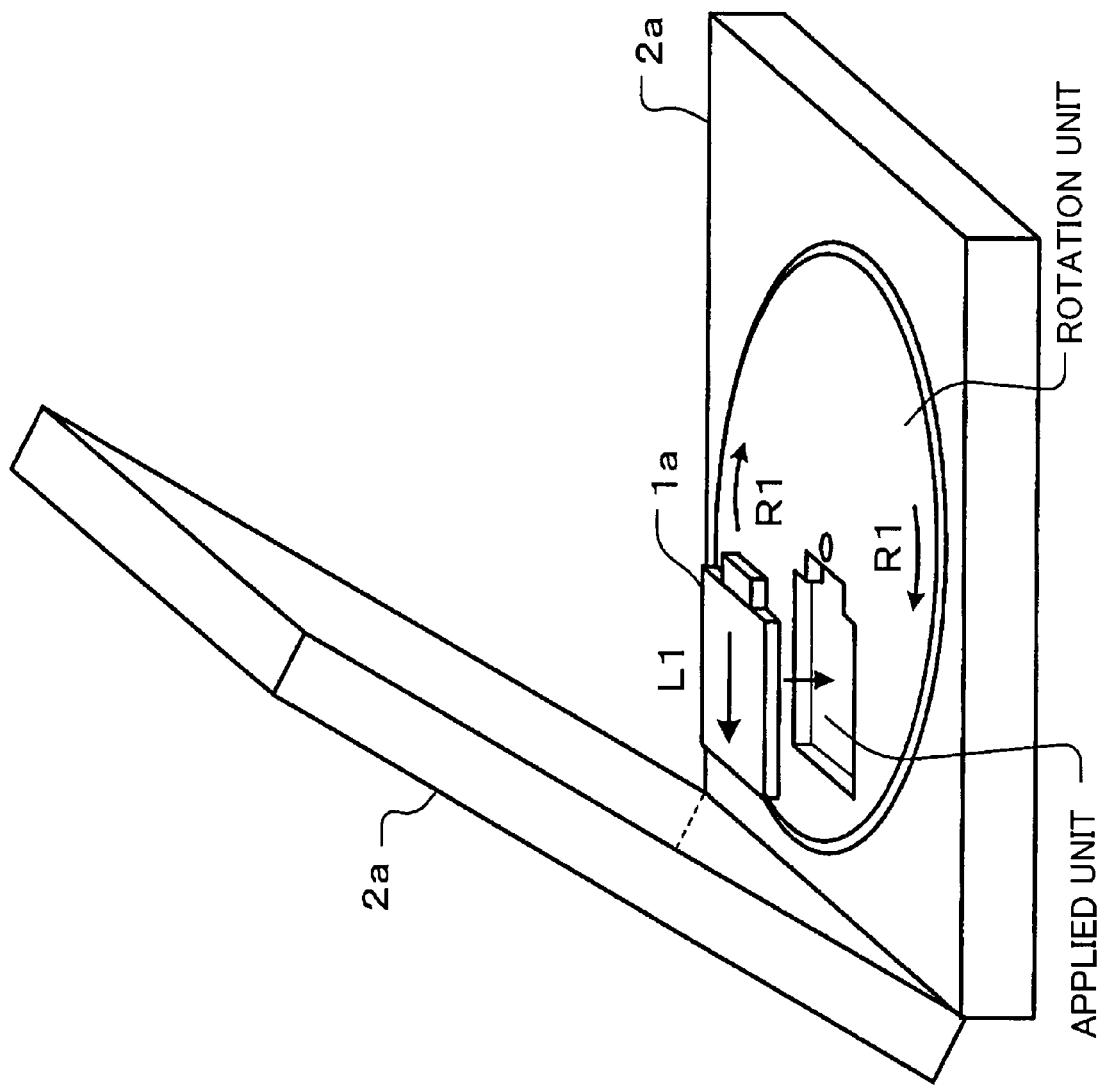
FIG. 8 is a view showing the other configuration of an isolation unit of a micro-cassette and the other configuration example of a micro-chemical analysis device according to the first embodiment.

Isolation unit 14 of micro-cassette 1 may generate the second sample in centrifuge separation method. In this case, as shown in FIG. 8, micro-cassette 1 comprises a check valve prevents the adverse current to the direction of sample processing unit 13 of micro-cassette 1, and a micro valve divides the first sample in half from sample processing unit 13. Micro-cassette 1a is fixed in analysis device 2a that consists of openable and closable two units that comprises a revolvable rotation unit in the direction of arrow line R1. The rotation unit rotates micro-cassette 1a so that centrifugal force may work at the direction of arrow line L1 that is direction of sample processing unit 13 to the first sample sent from sample processing unit 13 of micro-cassette 1 to isolation unit 14. The first sample in the isolation unit 14 of micro-cassette 1 separates to the second sample that consists of a useful component of dispensing unit 15 side and a formed element on the centrifuged sample processing unit 13 side. After the second sample is divided with the micro valve, the second sample divided is sent to dispensing unit 15.

Embodiment 2

Figure 9:
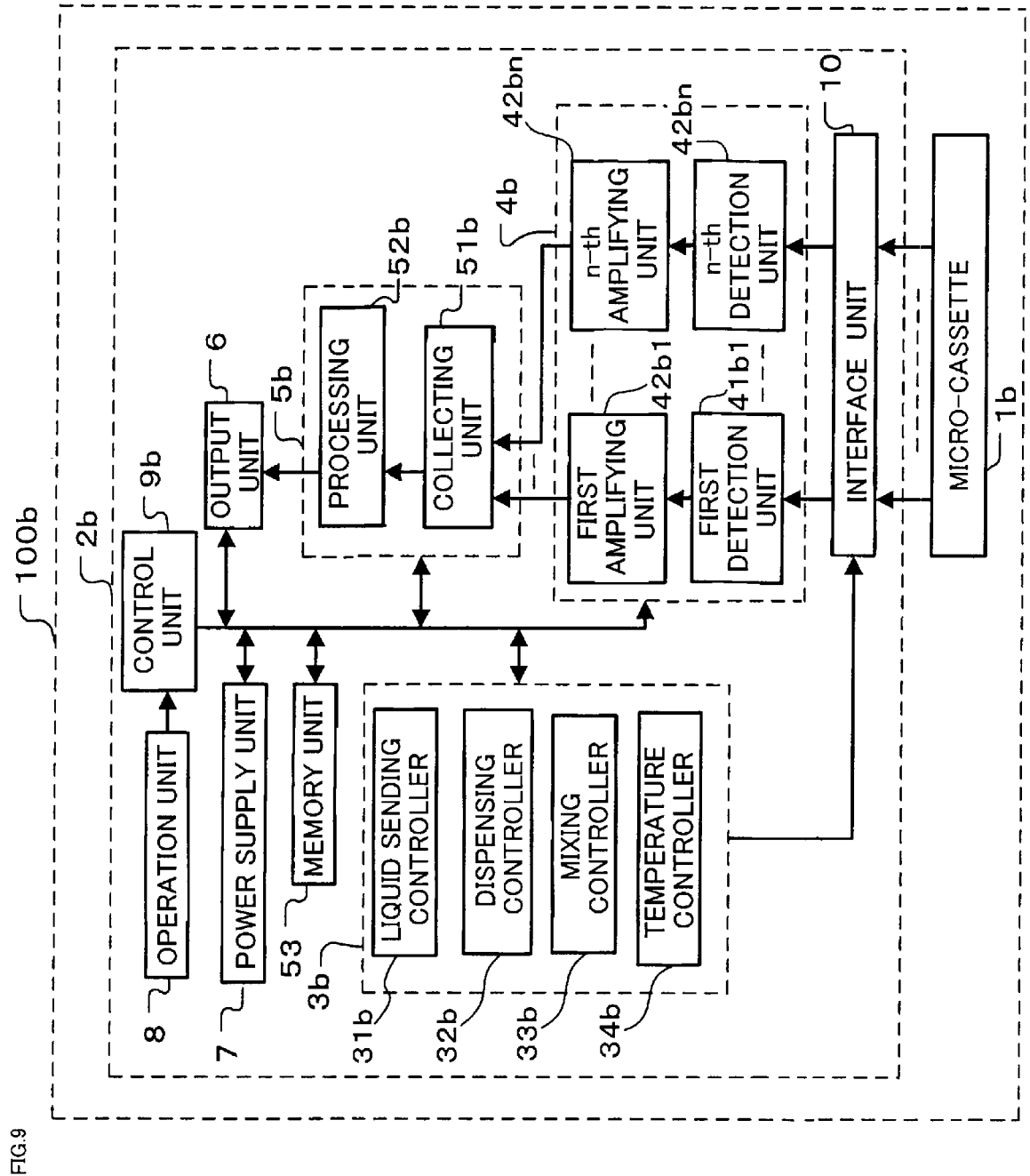
FIG. 9 is a block diagram showing a configuration of a micro-chemical analysis device according to the second embodiment.
Figure 10:
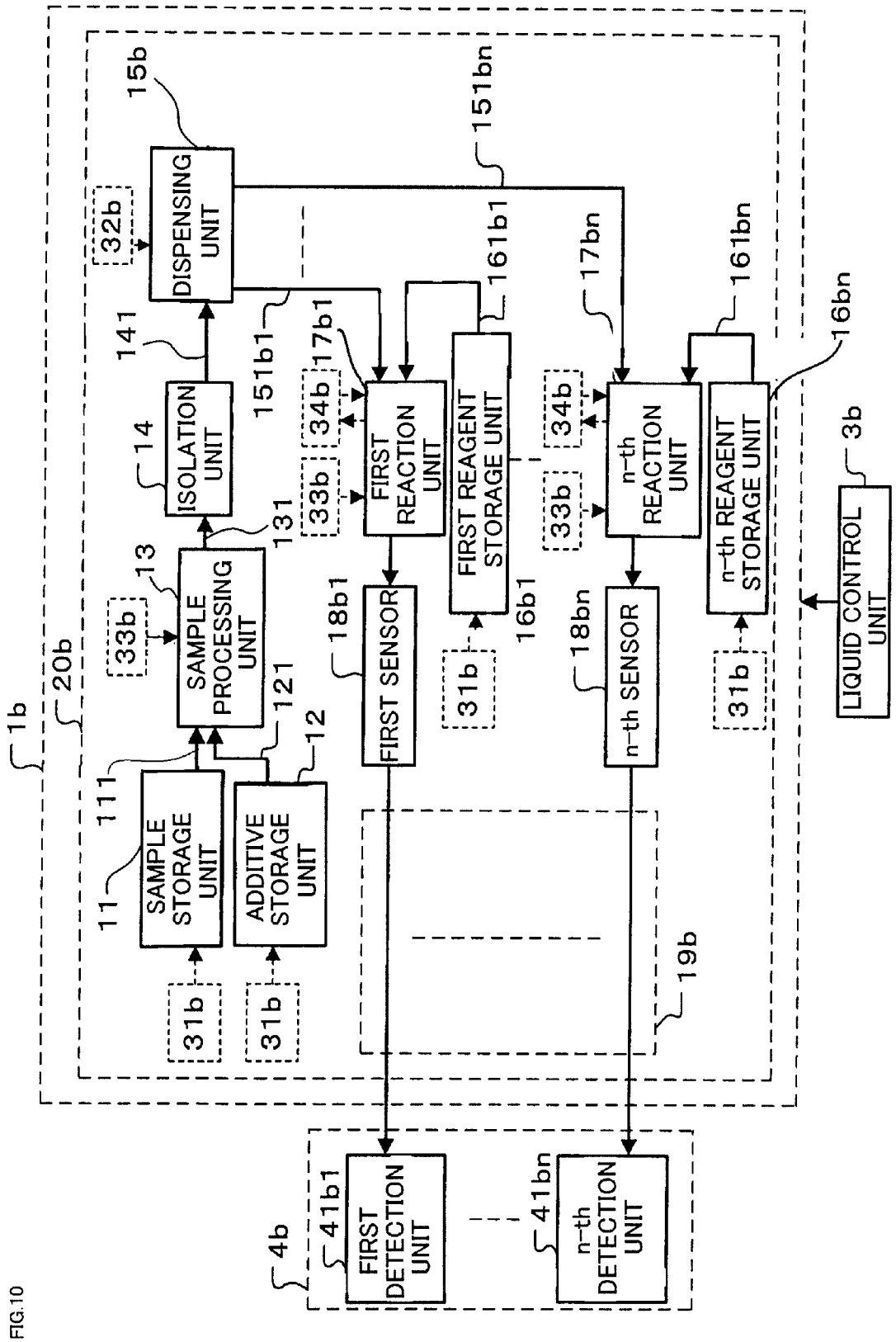
FIG. 10 is a view showing a configuration of a micro-cassette according to the second embodiment.

A second embodiment in accordance with the present invention will be explained with reference to FIGS. 9 and 10. FIG. 9 is a block diagram showing a configuration of a micro-chemical analysis device according to the second embodiment. FIG. 10 is a view showing a configuration of a micro-cassette according to the micro-chemical analysis device in FIG. 9.

The point where a second embodiment as shown in FIG. 10 is different from a first embodiment as shown in FIG. 3, the analysis unit 20 of the micro-cassette 1 comprises two or more reaction unit and the reagent storage unit send liquid to two or more reagent storage unit, with the dispensing unit where the second sample was dispensed into two or more reaction units.

The point where a second embodiment as shown in FIG. 9 is different from a first embodiment as shown in FIG. 1, the point is dispensing unit, two or more reagent storage unit, liquid control unit, and data processing unit. A similar unit to the first embodiment gives the same sign and omits explaining.

As shown in FIG. 9, micro-chemical analysis device 100b comprises micro-cassette 1b accommodates each liquid such as the sample, the additive, and the reagent that corresponds to plural measurement items, and analysis device 2b generates the analysis data detecting the signal generated with the measurement in micro-cassette 1b.

Analysis device 2b comprises interface unit 10 maintains micro-cassette 1b, liquid control unit 3b controls each liquid stored in the micro-cassette 1b, detection unit 4b detects the signal from micro-cassette 1b, data processing unit 5b generates the analysis data from the detection signal detected in detection unit 4b, memory unit 53 preserves the analysis data etc. generated in data processing unit 5b, output unit 6 outputs the analysis data generated in data processing unit 5b, power supply unit 7, and control unit 9b controls operation unit 8, liquid control unit 3b, detection unit 4b, data processing unit 5b, memory unit 53, output unit 6, and power supply unit 7.

Liquid control unit 3b comprises liquid sending controller 31b, dispensing controller 32b dispenses the second sample into plural reaction units in micro-cassette 1b, mixing controller 33b stirs the sample adds the additive or the compound liquid of the second sample in each reaction unit and the reagent, and temperature controller 34b sets the compound liquid in each reaction unit at a predefined temperature and maintains.

Detection unit 4b comprises the first to n-th detection unit 41b1 to 41bn detects the signal corresponding to each reaction unit output from micro-cassette 1b, and the first to n-th amplifying unit 42b1 to 42bn amplifies each detection signal from each the first to n-th detection unit 41b1 to 41bn to a predefined signal level. Detection unit 4b outputs each detection signal amplified in each first to n-th amplifying unit 42b1 to 42bn to data processing unit 5b.

Data processing unit 5b comprises collecting unit 51b generates each subject data from each detection signal output from each first to n-th amplifying unit 42b1 to 42bn of detection unit 4b, and processing unit 52b generates each analysis data from each subject data generated in collecting unit 51b.

FIG. 10 is a view showing a configuration of a micro-cassette. Micro-cassette 1b comprises storage unit stores each liquid, and analysis unit 20b is configured a leading each channel as for each storage unit.

Analysis unit 20b comprises sample storage unit 11, additive storage unit 12, sample processing unit 13, and isolation unit 14, sample channel 111, additive channel 121, processing channel 131, and isolation channel 141. Each channel leads between each unit.

Analysis unit 20b comprises dispensing unit 15b stored the second sample sent from isolation unit 14 to dispense, first to n-th reagent storage unit 16b1 to 16bn stores the first to n-th reagent, first to n-th reaction unit 17b1 to 17bn measures the compound liquid with each second sample from the dispensing unit 15b and each first to n-th reagent with first to n-th sensor, and connector 19b outputs each signal generated by the measurement with each first to n-th sensor 18b1 to 18bn to analysis device 2b.

Dispensing unit 15b leads to each first to n-th reaction unit 17b1 to 17bn through first to n-th dispensing channel 151b1 to 151bn. Each amount to which stored the second sample is set beforehand is sent to first to n-th reaction unit 17b1 to 17bn with dispensing controller 32b through each first to n-th dispensing channel 151b1 to 151bn.

First to n-th reagent storage unit 16b1 to 16bn lead to first to n-th reaction unit 17b1 to 17bn through each first to n-th reagent channel. Each first to n-th reagent of amount to which first to n-th reagent storage unit 16b1 to 16bn is set beforehand is sent to first to n-th reaction unit 17b1 to 17bn by liquid sending controller 31b that synchronizes with dispensing motion of the second sample.

Each compound liquid mixed in first to n-th reaction unit 17b1 to 17bn is maintained in a predefined temperature with temperature controller 34b of liquid control unit 3b of analysis device 2b located near micro-cassette 1b. Afterwards, each compound liquid is measured with first to n-th sensor 18b1 to 18bn. First to n-th sensor 18b1 to 18bn generates each signal corresponding to the density of each measurement item, and outputs the generated each signal to first to n-th detection unit 41b1 to 41bn of detection unit 4b of analysis device 2b through connector 19b. The sample, the additive, each reagent, and each compound liquid after the measurement ends is maintained in micro-cassette 1b.

Embodiment 3

Figure 11:
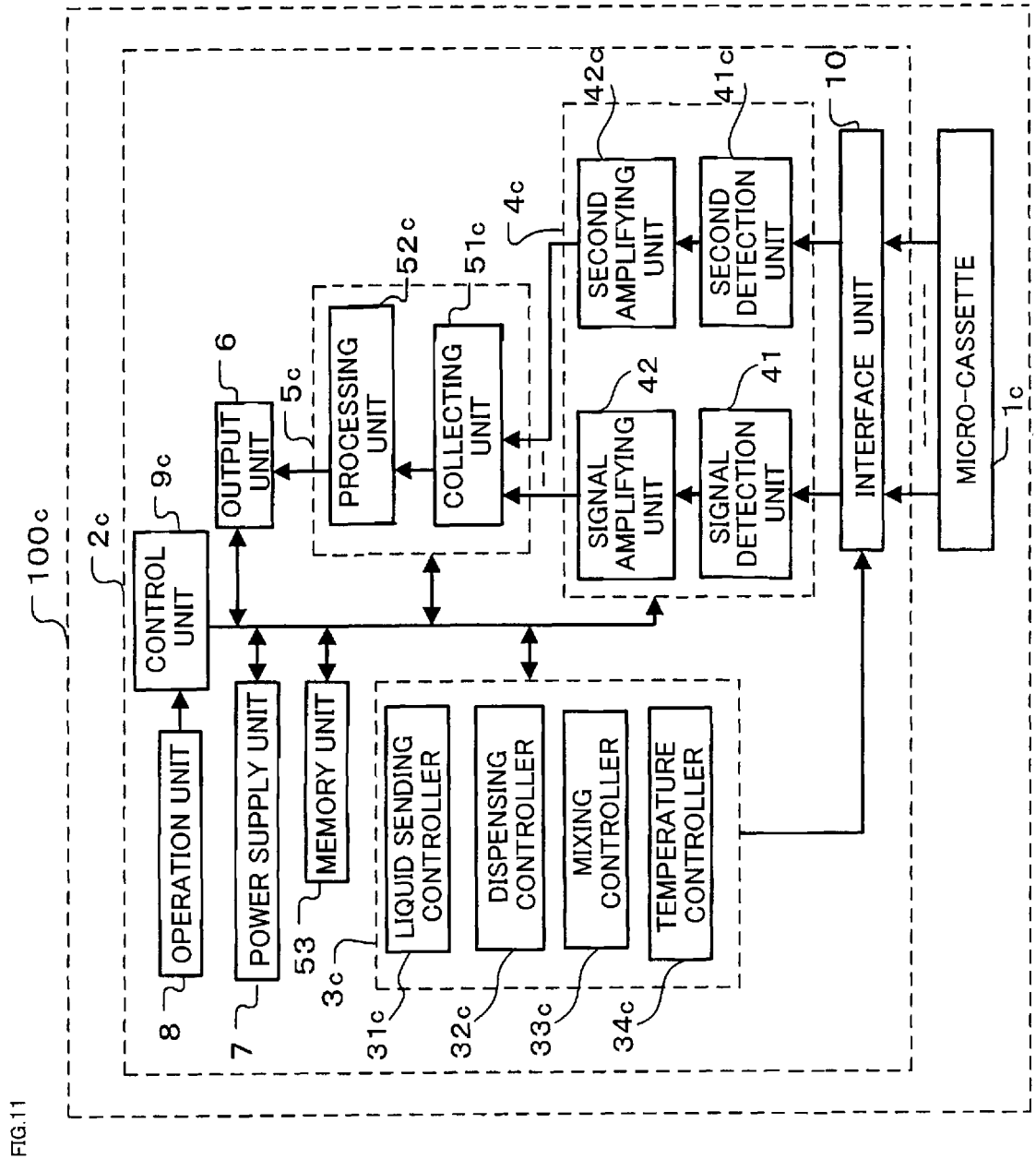
FIG. 11 is a block diagram showing a configuration of a micro-chemical analysis device according to the third embodiment.
Figure 12:
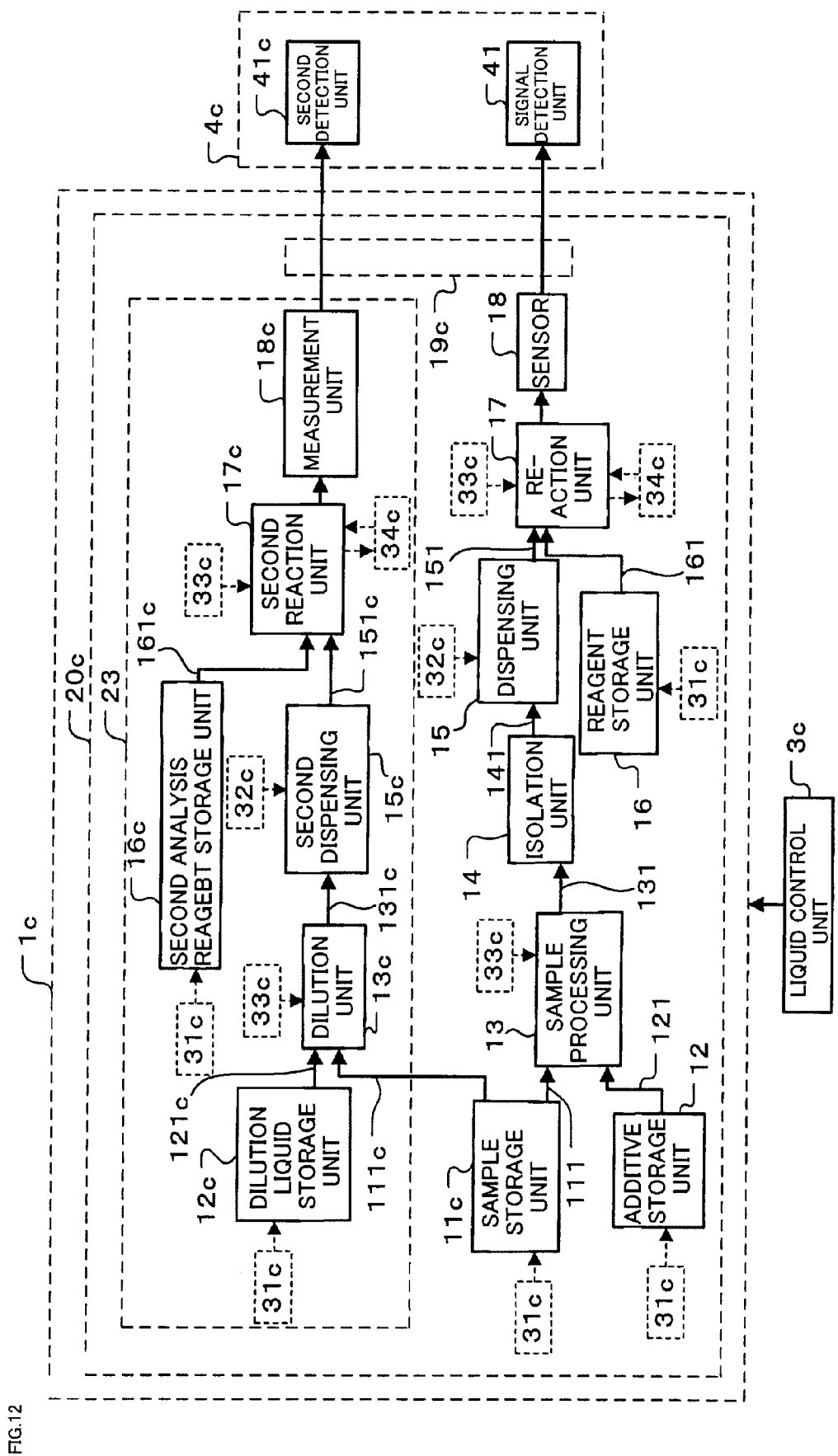
FIG. 12 is a view showing a configuration of a micro-cassette according to the third embodiment.

A third embodiment in accordance with the present invention will be explained with reference to FIGS. 11 and 12. FIG. 11 is a block diagram showing a configuration of a micro-chemical analysis device according to the third embodiment. FIG. 12 is a view showing a configuration of a micro-cassette used for micro-chemical analysis device.

The point where a third embodiment as shown in FIG. 12 is different from a first embodiment as shown in FIG. 3, the point is analysis unit 20 comprises second analysis unit in micro-cassette 1. The point where a second embodiment as shown in FIG. 12 is different from a first embodiment as shown in FIG. 1, the point is liquid control unit controls each liquid in second analysis unit, detection unit, and data processing unit. A similar unit to the first embodiment gives the same sign and omits explaining.

As shown in FIG. 11, microchemical analysis device 100c comprises micro-cassette 1c stores each liquid of the sample, the additive, the reagent, the dilution liquid that dilutes sample, and the second reagent that corresponds to measurement item of sample diluted with dilution liquid. Microchemical analysis device 100c comprises analysis device 2c generates each analysis data detecting each signal generated with the measurement in micro-cassette 1c.

Analysis device 2c comprises interface unit 10 maintains micro-cassette 1b, liquid control unit 3c controls each liquid stored in the micro-cassette 1c, detection unit 4c detects the signal from micro-cassette 1c, data processing unit 5c generates the analysis data from the detection signal detected in detection unit 4c, memory unit 53 preserves the analysis data etc. generated in data processing unit 5c, output unit 6 outputs the analysis data generated in data processing unit 5c, power supply unit 7 supplies the electric power to each unit of analysis device 2c, operation unit 8 inputs various command signals etc., and control unit 9c controls, liquid control unit 3c, detection unit 4c, data processing unit 5c, memory unit 53, output unit 6, and power supply unit 7.

Liquid control unit 3c comprises liquid sending controller 31b sends each liquid in micro-cassette 1c, dispensing controller 32c dispenses the second sample and diluted sample, mixing controller 33c stirs the compound liquid of the second sample and the reagent or the compound liquid of the diluted sample and the second reagent, and temperature controller 34c sets the compound liquid of the second sample and the reagent and the compound liquid of the diluted sample and the second reagent at a predefined temperature and maintains.

Detection unit 4c comprises the signal detection unit 41 and the second detection unit 41c detects the each signal output from micro-cassette 1b, and the signal amplifying unit 42 and the second amplifying unit 42c amplifies each detection signal from each the signal detection unit 41 and second detection unit 41c to a predefined signal level. Detection unit 4c outputs each detection signal amplified in each signal amplifying unit 42 and second amplifying unit 42c to data processing unit 5c.

Data processing unit 5c comprises collecting unit 51c generates each subject data from each detection signal output from signal amplifying unit 42 and second amplifying unit 42c of detection unit 4c, and processing unit 52c generates each analysis data from each subject data generated in collecting unit 51c.

As shown in FIG. 12, micro-cassette 1c comprises storage unit stores each liquid, and analysis unit 20c is configured a leading each channel as for each storage unit.

Analysis unit 20c comprises sample storage unit 11c, additive storage unit 12, sample processing unit 13, and isolation unit 14, reaction unit 17 has sensor 18, sample channel 111, additive channel 121, processing channel 131, isolation channel 141, dispensing channel 151. Each channel leads between each unit. Analysis unit 20c comprises second analysis unit 23 measures an impossible measurement item to measure in the second sample that weeds out the formed element contained in the first sample. For example, an impossible measurement item to measure is a blood count or a blood coagulation time included in blood.

Sample storage unit 11c leads to sample processing unit 13 through sample channel 111, and leads to second analysis unit 23 through second sample channel 111c. Sample of sample storage unit 11c is sent to sample processing unit 13 and second analysis unit 23 by liquid sending controller 31c.

Additive of additive storage unit 12 is sent to sample processing unit 13 by liquid sending controller 31c. Mixing controller 33c stirs the sample is sent to sample processing unit 13 and additive was added. Dispensing controller 32c dispenses the second sample that weeds out the formed element contained in the first sample and was stored in dispensing unit 15 to reaction unit 17. The reagent stored in reagent storage unit 16 is sent to a reaction unit 17 by liquid sending controller 31c. The compound liquid of the second sample and the reagent are mixed by mixing controller 33c in reaction unit 17.

Second analysis unit 23 comprises dilution liquid storage unit 12c stores the dilution liquid that dilutes the sample, dilution unit 13c dilutes the sample from sample storage unit 11c with the dilution liquid in dilution liquid storage unit 12c, the second dispensing unit 15c is stored to dispense the diluted sample from dilution unit 13c, second analysis reagent storage unit 16c stores the second reagent that corresponds to the measurement item, second reaction unit 17c has measurement unit 18c that measures the diluted sample is dispensed from second dispensing unit 15c and the compound liquid in second analysis reagent storage unit 16c.

Dilution liquid storage unit 12c leads to dilution unit 13c through dilution channel 121c. The dilution liquid of amount to which dilution liquid storage unit 12c is set beforehand is sent to dilution unit 13c by liquid sending controller 31c synchronizing with the sending operation of the sample to dilution unit 13c.

Dilution unit 13c has formed a Y-shaped that joins second sample channel 111c and dilution channel 121c. Dilution unit 13c leads to second dispensing unit 15c through dilution channel 131. The dilution liquid is mixed synchronizing with sending the sample in Y-shaped. Mixing controller mixes the compound liquid. The sample diluted by the mixture is sent to second dispensing unit 15c.

Second dispensing unit 15c leads to second reaction unit through second dispensing channel 151c. The amount to which the stored sample is set beforehand is sent to the second reaction unit 17c with dispensing controller 32c.

Second analysis reagent storage unit 16c leads to second reaction unit 17c through second analysis reagent channel 161c. The reagent of amount to which the second analysis reagent storage unit 16c is set beforehand is sent to second reaction unit 17c by liquid sending controller 31c that synchronizes with the dispensing operation of the sample.

Second analysis unit 17c has formed a Y-shaped channel that joins second dispensing channel 151c and second analysis reagent channel 161c. Second analysis unit 17c comprises measurement unit 18c measures the blood count or the blood coagulation time included in blood. After the sample joins the second reagent and mixes in the Y-shaped channel of second reaction unit 17c, the compound liquid is mixed by mixing controller 33c and becomes evenness.

The compound liquid mixed in the second reaction unit 17c is measured with measurement unit 18c.

Measurement unit 18c generates the signal such as the blood count or the blood coagulation time that is measurement item, and outputs the generated signal to detection unit 4c and second detection unit 41c through connector 19c. The sample, the additive, the reagent, the dilution liquid, the second reagent, and the compound liquid after the measurement ends are maintained in the micro-cassette 1c.

Embodiment 4

Figure 13:
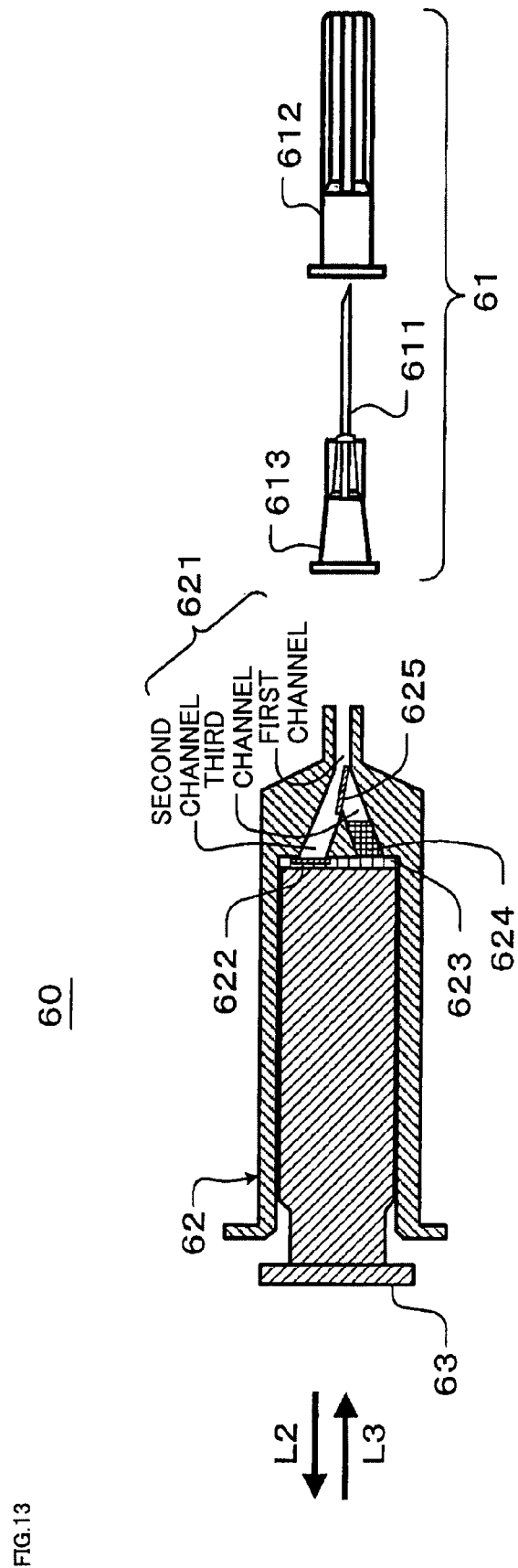
FIG. 13 is a view showing a configuration of a sample-collecting tool according to the fourth embodiment.
Figure 14:
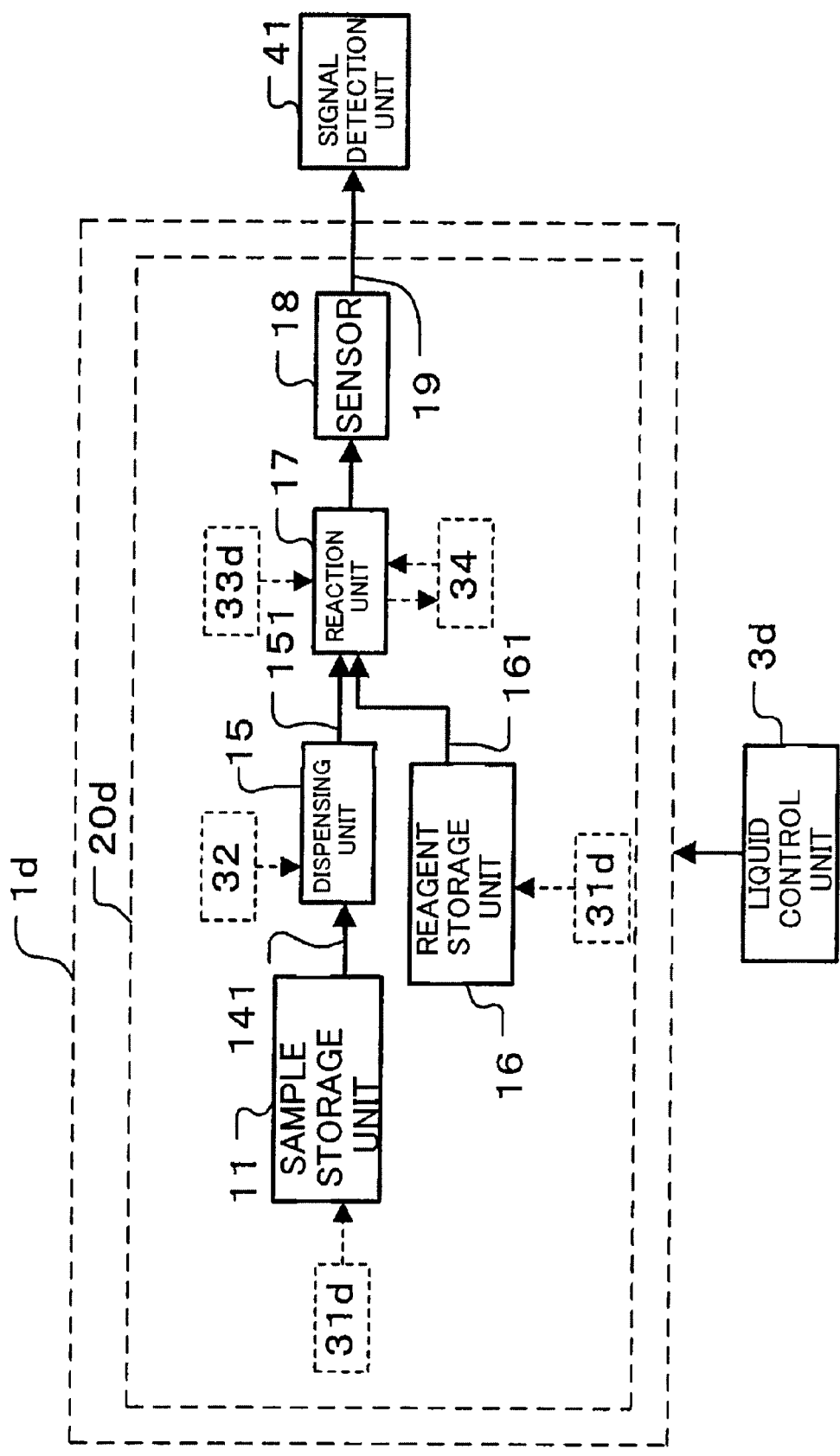
FIG. 14 is a view showing a configuration of a micro-cassette according to the fourth embodiment.
Figure 15:
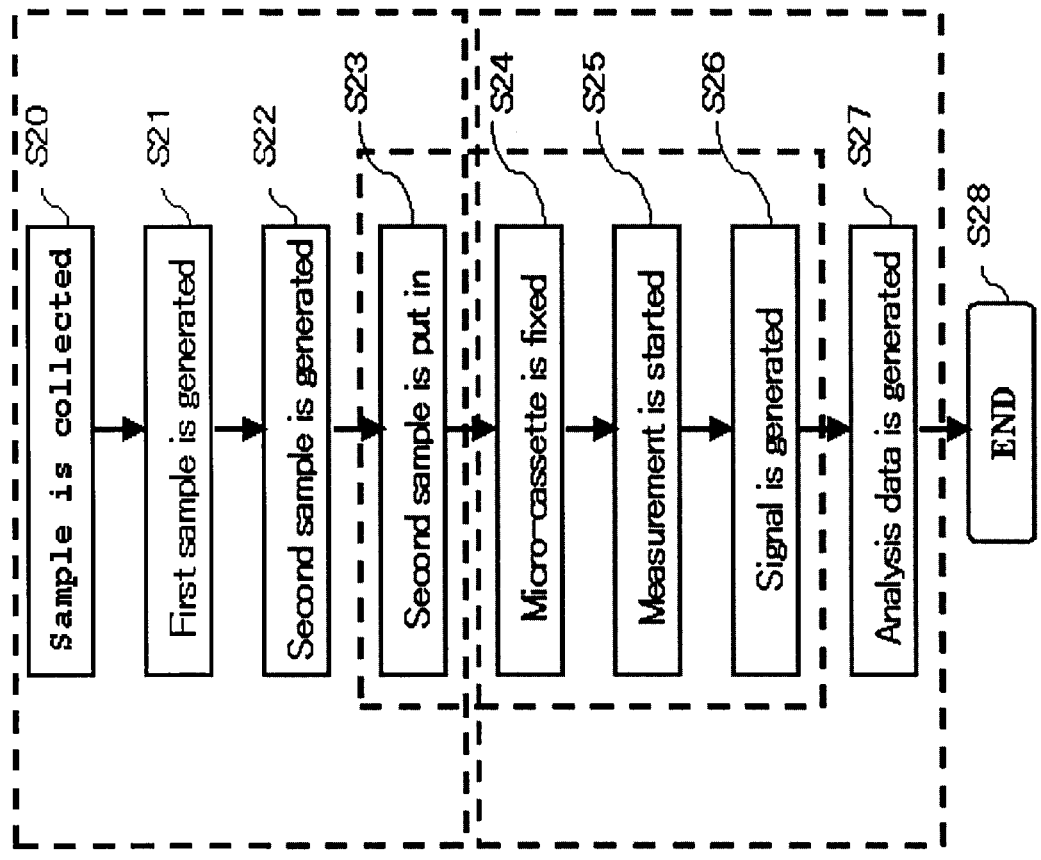
FIG. 15 is a flow chart showing an operation of using a sample-collecting tool according to the fourth embodiment.

A fourth embodiment in accordance with the present invention will be explained with reference to FIGS. 13 to 15. FIG. 13 is a view showing a configuration of a sample-collecting tool according to the fourth embodiment. FIG. 14 is a view showing a configuration of a micro-cassette according to the fourth embodiment. FIG. 15 is a flow chart showing an operation of using a sample-collecting tool according to the fourth embodiment.

As shown in FIG. 13, sample collecting tool 60 comprises needle unit 61 collects the sample, cylindrical cylinder 62 shown in cross section where sample is stored by needle unit 61, and piston 63 sucks in the sample from needle unit 61 in cylinder 62, and spews the sucked sample from needle unit 61.

Piston 63 is stored slidably in the direction of arrow line L2 and L3 in cylinder 62.

For example, when the sample is blood, needle unit 61 comprises needle 611 is inserted in the blood vessel of subject, cap 612 prevents the piercing damage to the operator by needle 611 of the sample collecting tool 60, needle hub 613 maintains the cap 612 in removable and maintains needle 611. Needle hub 613 maintains needle 611 in the part, connects with the part of cylinder 62 in the other end part.

Neighborhood of a part in cylinder 62 comprises Y-shaped channel 621 is passed that sample flows in and flows out through needle unit 61, inflow valve 622 flows in the sample that passed Y-shaped in cylinder 62, the additive generates the first sample from the sample that flows in from Y-shaped in cylinder 62 through inflow valve 622, filtration film 624 generates the second sample from the first sample generated with the additive, outflow valve 625 flows out the second sample in the cylinder by filtration film 624 the second sample generated.

Y-shaped channel 621 is composed by the first to the third channel. Y-shaped channel 621 comprises the first channel in a part of cylinder 62 connected with needle hub 613 in needle unit 61.

When piston 63 does slide in the direction of L2, the sample sucked from needle 611 in needle unit 61 flows in via the second channel after passes over the first channel to cylinder 62. When piston 63 does slide in the direction of L3, the sample in cylinder 62 is spewed from needle 611 via the first channel after it passes over the second channel.

Inflow valve is arranged at the exit of the second channel of Y-shape channel. Inflow valve is opened by the slide to the direction of L2 of piston 62, and shuts with the slide to the direction of L3 of piston 62.

Additive 623 stores in cylinder 62, and generated the first sample that is corporealized useless component that negatively affects measurement with micro-chemical analysis device of the component contained in sample that flows in cylinder.

Filtration film 624 is maintained in the third channel of Y-shaped channel, separates the formed element in the first sample that has flowed out to the third channel and generates the second sample.

Outflow valve 625 is arranged at the exit of the third channel that joins each channel of Y-shaped channel 621. Outflow valve 625 is opened by the slide to the direction of L3 of the piston 63, and shuts with the slide to the direction of L2 of the piston 63.

The fourth embodiment shown in FIG. 14 differ from the first embodiment shown in FIG. 3 that the sample storage unit 11 in analysis unit 20d of micro-cassette 1 is connected with dispensing unit 15 through direct channel 141.

As shown in FIG. 14, liquid control unit 3d comprises liquid sending controller 31d sends the second sample that was spewed from sample collecting tool 60 of FIG. 13 and stored in the micro-cassette 1d, dispensing controller 32, mixing controller 33d mixes the compound liquid of the reagent and the second sample, temperature controller 34. A similar unit to the first embodiment of each unit concerning the fourth embodiment gives the same code and omits explaining.

It explains the measurement procedure when sample collecting tool 60 is used with FIG. 15.

The sample is sucked to the cylinder 62 from the needle unit 61 by using sample collecting tool 60 in FIG. 13 (S20). In sample collecting tool 60, the sample that flows in cylinder 62 from Y-shaped channel 621 through inflow valve 622 is mixed with the additive and generates the first sample that corporealized useless component that negatively affects measurement (S21). The first sample passes filtration film 624 in sample collecting tool 60. A useless formed element is separated with filtration film and the second sample is generated (S22).

A predefined amount of the second sample is put in to sample storage unit 11 of micro-cassette 1d in FIG. 14 from sample collecting tool 60 (S23). Micro-cassette 1d is put in the second sample is fixed in micro-chemical analysis device 100 (S24). The operator puts in the second sample to micro-cassette 1d, and fixes micro-cassette 1d in micro-chemical analysis device 100.

When micro-cassette 1d is fixed in micro-chemical analysis device 100, micro-chemical analysis device 100 automatically begins measuring (S25).

Dispensing controller 32 dispenses the second sample from isolation unit 14 to reaction unit 17 through dispensing channel 151. Liquid sending controller 31 sends the reagent in reagent storage unit 16 to reaction unit 17 through reagent channel 161. Mixing controller 33 mixes the compound liquid of the second sample sent from dispensing unit 15 and the reagent sent from reagent storage unit 16. Temperature controller 34 sets at a predefined temperature and maintains the compound liquid. Sensor 18 generates the signal corresponding to the component density of the measurement item measuring the compound liquid maintained at a predefined temperature, and outputs the generated signal to detection unit 4 of analysis device 2 through connector 19 (S26).

Detection unit 4 of signal detection unit 41 outputs to the signal amplifying unit 42 detecting the signal output through connector 19 of micro-cassette 1d. The detection signal output from signal detection unit 41 is amplified to a predefined signal level and the signal amplifying unit 42 is output to data processing unit 5.

Collecting unit 51 in data processing unit 5 generates the subject data from the detection signal output from signal amplifying unit 42, and outputs it to processing unit 52. Processing unit 52 reads out the calibration table of the measurement item from memory unit 53 to the subject data output from collecting unit 51. Processing unit 52 generates the analysis data of the component density etc. of the measurement item contained in the sample by using the read out calibration table, and the generated analysis data is preserved in memory unit and outputs it to output unit 6 (S27).

When the analysis data is output to output unit 6, control unit 9 directs the stop of measurement motion of liquid control unit 3, detection unit 4, data processing unit 5, memory unit 53, and output unit 6, and micro-chemical analysis device 100 ends the measurement (S28).

After the measurement ends, the operator takes out micro-cassette 1d where each liquid that ends measurement is stored, and abandons micro-cassette 1d taken out. By sample collecting tool 60 of the composition shown in FIG. 13, the composition of analysis unit 20 of micro-cassette 1d can be simplified because analysis unit 20 doesn't need sample channel to generate the first and second sample, additive storage unit, additive channel, sample processing unit, processing channel, and isolation unit. The composition of liquid control unit of analysis device 2 can be simplified because liquid control unit doesn't need the control of the liquid such as sending the additive and first sample and mixture of the sample and additive.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A micro-chemical analysis device, comprising:
    a detachable micro-cassette including a sample storage unit containing an original sample, a reagent storage unit containing a reagent, and an additive storage unit configured to store an additive; and
    an analysis device configured to receive the detachable micro-cassette containing the original sample and the reagent, wherein
    the analysis device includes
        a liquid control unit configured to cause the original sample contained in the sample storage unit to be transferred to a sample processing unit of the micro-cassette through a sample channel, and to cause the additive stored in the additive storage unit to be transferred to the sample processing unit of the micro-cassette through an additive channel;
    the micro-cassette includes
        the sample processing unit configured to mix the additive to the original sample to form a waste component that negatively affects analysis of the original sample so as to obtain a first sample and the waste component, the mixing of the additive and the original sample being controlled by the liquid control unit of the analysis device; and
        an isolation unit configured to separate the waste component from the first sample to produce an isolated second sample; and
    the analysis device further includes
        a data processing unit configured to produce analysis data indicative of a component of interest included in a mixture of the isolated second sample and the reagent.

2. The micro-chemical analysis device according to claim 1, wherein the isolation unit comprises a filtration film disposed in the micro-cassette and configured to filter the sample.

3. The micro-chemical analysis device according to claim 1, wherein the isolation unit comprises a centrifugal device disposed in the analysis device and configured to rotate the micro-cassette.

4. The micro-chemical analysis device according to claim 1,
    wherein micro-cassette contains first and second reagents, and the data processing unit is configured to produce a first analysis data indicative of a first component of interest included in a mixture of the original sample and the first reagent and a second analysis data indicative of a second component of interest included in a mixture of the original sample and the second reagent.

5. The micro-chemical analysis device according to claim 1, further comprising a main body including plural insertion parts configured to receive respective plural detachable micro-cassettes, wherein the data processing unit is configured to generate plural analysis data corresponding to plural components of interest produced in processing samples and reagents contained in the plural micro-cassettes inserted in the insertion parts.

6. The micro-chemical analysis device according to claim 1, wherein the micro-cassette contains first and second original samples and first and second reagents, and the data processing unit is configured to produce first analysis data indicative of a first component of interest included in a mixture of the first original sample and the first reagent and second analysis data indicative of a second component of interest included in a mixture of the second original sample and the second reagent.

7. The micro-chemical analysis device according to claim 1, wherein the original sample is blood contained by the micro-cassette, and the micro-cassette includes a measurement unit that measures a coagulation time of the blood or a blood count in the blood.

8. The micro-chemical analysis device according to claim 1, wherein the data processing unit is configured to produce analysis data indicative of the component of interest, which is one of protein, carbohydrate, and fat contained in blood.

9. The micro-chemical analysis device of claim 1, wherein the liquid control unit is configured to cause the first sample to be sent from the sample processing unit to the isolation unit, to dispense the second sample from the isolation unit to a reaction unit, to cause the reagent contained in the reagent storage unit to be sent to the reaction unit, and to cause the reagent and the second sample to be mixed in the reaction unit.

10. The micro-chemical analysis device of claim 1, wherein the liquid control unit comprises:
    a mixing controller configured to cause the reagent and the second sample to be mixed in a reaction unit to form a compound liquid.

11. The micro-chemical analysis device of claim 10, wherein the liquid control unit comprises:
    a temperature controller configured to maintain the compound liquid in the reaction unit at a predefined temperature.

12. The micro-chemical analysis device of claim 1, wherein the liquid control unit is further configured to cause the additive to be transferred to the sample processing unit in synchronization with a transferring motion of the sample.

* * * * *